United States Patent [19]
Manning et al.

[11] Patent Number: 5,106,647
[45] Date of Patent: * Apr. 21, 1992

[54] METHOD TO MANUFACTURE GAS MONITORING TEST STRIPS

[75] Inventors: Charles R. Manning, Palo Alto; Leroy J. Pinto, Los Altos, both of Calif.

[73] Assignee: Assay Tec Associates, Inc., Palo Alto, Calif.

[*] Notice: The portion of the term of this patent subsequent to Aug. 7, 2007 has been disclaimed.

[21] Appl. No.: 562,718

[22] Filed: Aug. 6, 1990

Related U.S. Application Data

[60] Continuation of Ser. No. 275,346, Nov. 23, 1988, Pat. No. 4,946,705, which is a division of Ser. No. 43,921, Apr. 29, 1987, abandoned, which is a continuation-in-part of Ser. No. 644,762, Aug. 27, 1984, abandoned, which is a continuation-in-part of Ser. No. 644,761, Aug. 27, 1984, abandoned, which is a continuation-in-part of Ser. No. 354,497, Mar. 3, 1982, abandoned.

[51] Int. Cl.$^5$ ............................................. A01N 1/02
[52] U.S. Cl. .......................................... 427/2; 422/56; 422/57
[58] Field of Search ............................ 422/55-58, 422/83, 86, 87; 427/2; 436/1, 93

[56] References Cited

U.S. PATENT DOCUMENTS 4,946,705 8/1990 Manning et al. .................... 427/2

Primary Examiner—Michael Lusignan
Attorney, Agent, or Firm—Morrison & Foerster

[57] ABSTRACT

A simple, inexpensive, and versatile device for measuring gaseous substances and a method for manufacture of such devices are described. The device comprises a reflectant backing upon which is disposed a layer which is composed of microparticles coated with a reagent and then with a diffusion layer which contains a diffusion moderator and binder, and optionally a plasticizer. A variety of useful configurations of this device are described.

7 Claims, 5 Drawing Sheets

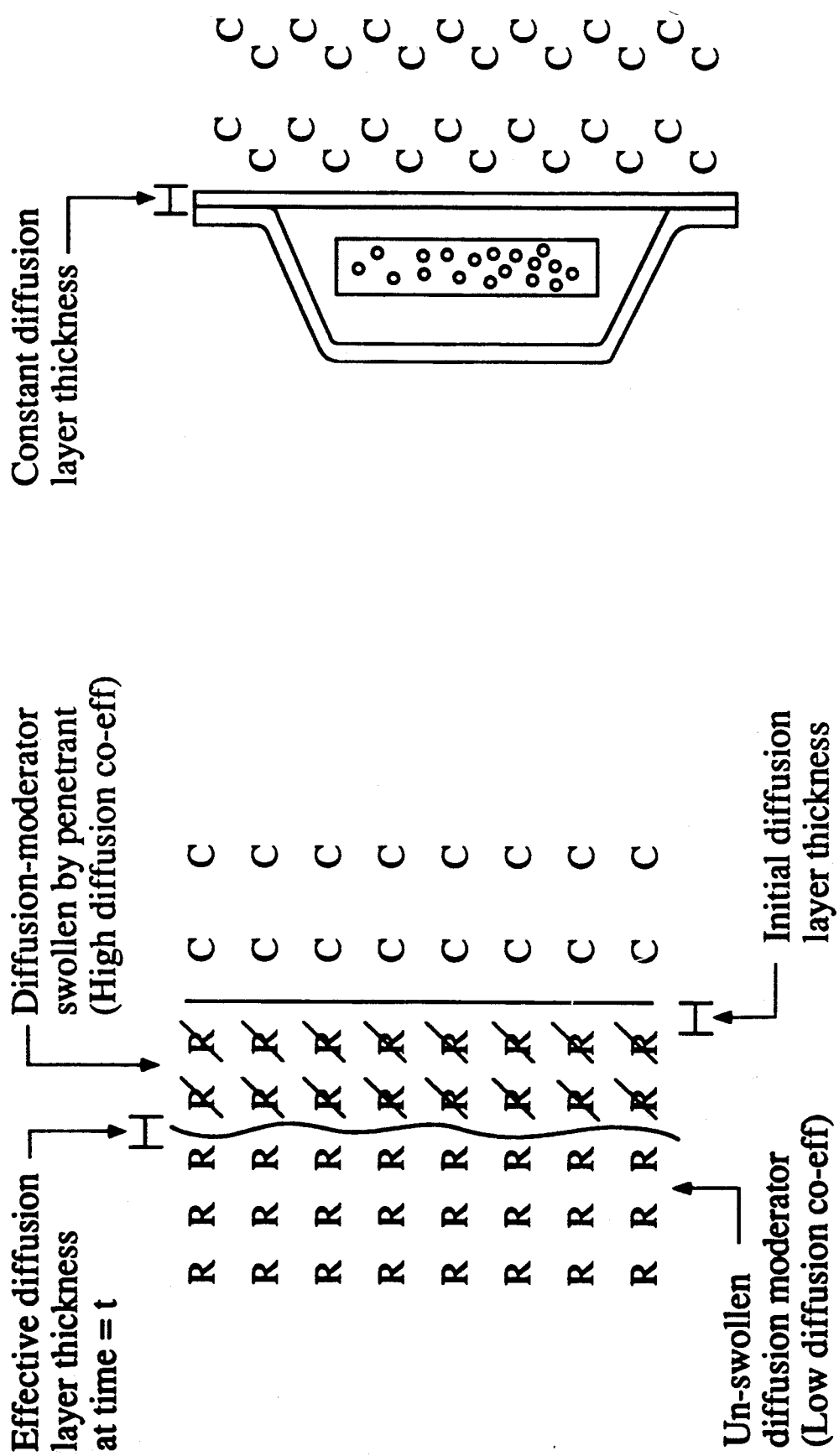

METHOD TO MANUFACTURE GAS MONITORING TEST STRIPS

This application is a continuation of U.S. Ser. No. 07/275,346, filed 23 November 1988, now U.S. Pat. No. 4,946,705, which is a divisional of U.S. Ser. No. 07/043,921, filed 29 April 1987, now abandoned, which is a continuation-in-part of U.S. Ser. No. 06/644,762 and of U.S. Ser. No. 644,761, both filed 27 August 1984 and both now abandoned, which applications are continuations-in-part of U.S. Ser. No. 354,497, filed 3 March 1982, now abandoned.

TECHNICAL FIELD

This invention relates to the field of measuring exposure to chemical substances and to devices which quantify gaseous substances in the environment. More specifically, it relates to simplifying toxic gas dosimetry by integrating means for collection, storage, signal development and read-out into a single economical device.

BACKGROUND ART

Workers in a variety of environments, such as hospitals, factories and institutions of learning may be exposed depending on the circumstances to a variety of noxious gases at low concentrations. A number of such commonly encountered vapors are listed by Saxe, I.N. *Dangerous properties of Industrial Materials*, 5th Ed.. Van Nostrand Reinhold Co., N.Y. (1979) as particular problems in the technologically sophisticated environments of developed countries. Also, lists of hazardous trace substances present in work places and in the general environment in the U.S. are published periodically by the Occupational Safety and Health Administration and by the Environmental protection Agency in the Federal Register. Contaminating gases include ethylene oxide, formaldehyde, sulfur dioxide, carbon monoxide, hydrogen sulfide, nitrogen oxides, peroxides, acidic gases, arsine and phosphine, ozone, and halogens. This list, of course, is not limiting or all inclusive but includes those substances that may be found in reasonably low concentrations, i.e., in the ppm or ppb ranges, where prolonged exposure constitutes a hazard.

It is well understood currently that persons in environments where even permitted levels of the above gases exist must be monitored for exposure. The time-average concentration or dose applied over time is particularly important since this parameter correlates strongly with the effect on the exposed individual. Accordingly, there have been many attempts to design devices which are capable of assaying total exposure to an individual or to a particular location. Many of these methods involve bulky collection systems such as cartridges providing passage through adsorbents such as charcoal or solvents, or complex-to-manufacture diffusion devices. See, for example, *NIOSH Manual of Analytical Methods*, 2nd Ed. Pt 1-NIOSH Monitoring Methods NIOSH 77-157-A. and U.S. Pat. Nos. 3,985,017 and 3,924,219. The portable portions of these devices are simply for collection and storage, and the procedures for signal development and readout require skilled personnel and independent instrumentation.

In most instances, the collection device is, in fact, separate from the detection system. The desired material is extracted from the device, and the chemistry which permits detection of the target gas by development of a color or by other means is performed separately. This generally involves the use of instrumentation with concomitant investment of time and facilities, capital investment, and commitment of skilled personnel.

The only devices presently commercially available which attempt to integrate the detection chemistry with the collection device involve complex and expensive collector systems attached to development reagents enclosed in plastic bags. (See U.S. Pat. No. 4,208,371.) The plastic bags are then squeezed into a configuration suitable for reading in a colorimeter. In many cases additional reagents are required which must be freshly made in the laboratory. No device currently exists which is capable of accurately assessing total dosage or time weighted average exposure at low levels that is simple, inexpensive, and capable of immediate quantitative readout by non-expert personnel.

DISCLOSURE OF THE INVENTION

The present invention offers a simple, economical and effective device for identifying and quantifying low levels of exposure to environmental contaminants, and a simple process for the manufacture of the device. The device can be worn as a badge, attached to equipment or furnishings, or otherwise mounted in the monitored environment. It integrates collection, storage, signal development and readout onto a single, inexpensive article, which requires only contact with a developing solution and the assistance of a simple reflectance meter to obtain quantitative results.

The device utilizes a reflecting backing material to which is adhered a layer composed of microparticles which are impermeable to the gas analyte material. The particles are coated with a "collection layer" which includes a behaviorally uniform diffusion layer through which the gas molecules must diffuse in order to reach the microparticle surface at which surface lies a reagent for detection. The structure of the totality of the particle-supported collection layer is such that it has characteristics of a true dosimeter, i.e., it responds to time weighted average concentration. Accordingly, the diffusion layer is in contact with a reagent or reagents which is/are coated onto the microparticles and which is/are specific for the analyte to be measured. The analyte, thus, diffuses through the diffusion layer to the surface of the microparticles where the reagent system entraps the analyte and preserves it for future analysis. The trapping reagent is preferably one of the reagents used in the detecting reaction although a second reagent may subsequently be added to develop the readable signal. The "collection layer." therefore, is capable of accumulating analyte in a time-dependent manner, so that it becomes a true dosimeter—i.e., it represents the integral of (concentration) x (time interval) over a certain exposure time.

Depending on the chemistry of the detecting reaction, it may be desirable to cover the collection layer with a retractable transparent cover slip which is resistant to ultraviolet light and penetration by certain gases or the detecting device may be further protected by encasing it in a semipermeable envelope. The cover slip or envelope serves to protect the collection layer from contamination by particulates and to provide an enclosed holder for wet reagents so as to protect the reflectance meter, but, also important, it prevents the alteration of the characteristics of the detection device by water vapor and deterioration of the product of the detecting reaction via light- or oxygen-catalyzed degradation after the detecting reaction is permitted to take place. The detecting reaction may typically be completed by dipping or spraying the device so that the particles contact a solution containing an additional reagent required to form a substance which is perceivable by eye and/or quantifiable by instrumentation.

Thus, in one aspect, the invention relates to a device for quantifying exposure to-a gaseous substance which device comprises a reflectant, non-porous. Planar backing, and a reflectant, microparticulate adsorbent support, upon which microparticulate support is disposed first, a coating of a reagent specifically reactive with analyte, surrounded by a diffusion layer permitting diffusion of the gaseous substance through it, and which diffusion layer comprises a diffusion moderator, a binder, and, optionally, a plasticizer. In some preferred embodiments, the foregoing device additionally contains a transparent, relatively non-porous, flexible, planar coverslip attached to the backing, and disposed flexibly over the microparticles coated with the collection layer. This cover slip is permeable to the desired analyte but not to interfering substances, especially water. Alternatively, the entire device is encapsulated in an envelope with these properties.

In other aspects, the invention relates to methods for manufacture of the device of the invention, and to methods for measuring the exposure to gaseous substances using this device.

BRIEF DESCRIPTION OF THE DRAWINGS

FIG. 3 shows the device of FIG. 2 modified by the analyte to be measured so as to exhibit case II diffusion.

FIG. 4 shows the measuring device represented in FIG. 2 surrounded by a controlling constant thickness diffusion layer.

MODES OF CARRYING OUT THE INVENTION

A. Definitions

Figure 1:
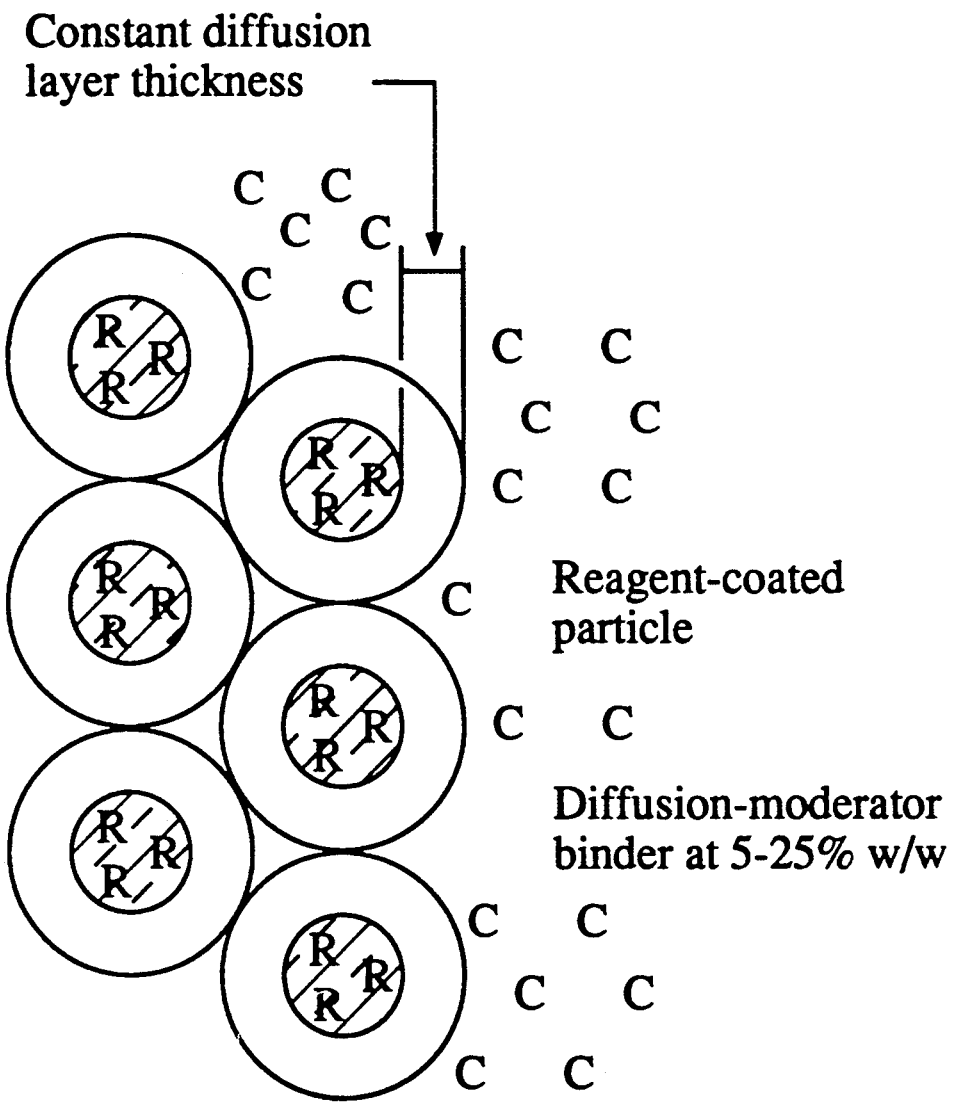
FIG. 1 shows, diagramatically, a portion of the layer of microparticles of the device of the invention.

As used herein, "quantifying exposure" specifically refers to obtaining a measure of the total dosage for a material which represents the integral of the product of concentration × time over the series of times of interest. Thus, since the device "quantifies exposure" it behaves as a true dosimeter. It measures the time weighted average exposure as defined by the American Conference of Government International Hygienists. National Institute of occupational Safety and Health, and the occupational Safety and Health Administration.

In their definition, a true dosimeter must respond to the integral $\int^t_0 Cdt$ even for complex variations in concentration of the analyte. For example, if the concentration of the analyte varies with time, the response to the true dosimeter will be directly proportional to this integral, despite the complexity of the time dependence of the concentration.

Thus, the device must accumulate response to the gas concentration on a continuous basis without changing as a result of the total length of time exposed, or the relative humidity, or other factors which would cause deviation of the measured response from being directly proportional to this integral.

"Reflectant" refers to a property related to the reflection of a light beam wherein the ratio of intensity of the reflected beam to that of the incident beam approaches 1. No particular absolute cut-off value such as, for example 99%, can be given since capacities to reflect represent a continuum. Use of this term, therefore, relates to a functional definition where there is sufficient light reflected to accomplish the purposes of the analysis.

"Non-porous" refers to a substance which does not permit the collection into it of gas molecules in substantial amount.

"Collection layer" refers to the coating on the microparticles of the device of the invention which exhibits such diffusion, surface and storage characteristics that it behaves as a true dosimeter. Collection layer is used, as will be clear from the context, to refer to the coating of a single particle or to the totality of such coatings. The "collection layer" on each microparticle has two parts. The reagent at the surface of the microparticles is capable of trapping the diffused gas molecules by reaction with the gas. The diffusion layer surrounding the reagent comprises a diffusion moderator and a binder. The diffusion moderator and binder are often the same material.

"Diffusion moderator" refers to the component of the diffusion layer which controls the uptake of the substance to be measured by creating a patina of constant thickness through which the substance must diffuse. This imparts the characteristic response of a true dosimeter—i.e., proportional to the integrated product of concentration and exposure time.

"Specific reagent" refers to a reagent which reacts with the analyte or gas desired to be measured, but with no other substances which are present in the environment being assessed and capable of transversing the diffusion layer. In this sense, "specific reagent" also has a functional definition—i.e., if reactivity is exclusive to the desired analyte in the environment where measurements are to take lace, it is sufficiently specific for purposes of the device and methods of the invention.

"Transparent," like reflectant, has a functional definition. It refers to a material wherein the ratio of intensities of the exit beam to the incident beam approaches 1, but a specific numerical limit is meaningless. As long as the material is sufficiently transparent to permit the analysis to yield results, it will meet the definition.

"Colored product" refers to a material which absorbs light of selected wavelengths. It is intended to include both wavelengths resulting in a color visible to the unaided eye and to the absorption of wavelength outside the visible range but amenable to simple instrumentation. Thus "colored product" also refers for example, to materials which absorb in the near ultraviolet.

"Microparticulate" support refers to particles which are reflectant, and finely divided so as to expose a large amount of surface area for coating with collection layers. The size of the particles is inversely proportional to the sensitivity of the device, since more surface area imparts more sensitivity to the test. Sizes of particles in the range capable of prociding 10-1000 m²/g are suitable for uses in the invention, but this range is not taken to be limiting. Larger particle sizes are workable but decrease the sensitivity. Smaller particles are desirable from the standpoint of sensitivity, but may be less convenient to handle. Any workable surface area/mass ratio is within the scope of the invention, and the suggested range is merely intended to provide guidance to practitioners thereof.

B. General Description

In general approach, the invention seeks to provide a simple device for measuring total dosage of a gaseous analyte by providing a diffusion medium interface with the capacity to entrap molecules of the gas to be measured. This diffusion layer is disposed on a reflectant particulate support coated with specific reagent and applied to a planar backing so that the development of a colored product can be quantified using a standard reflectance spectrophotometer. If the colored product is not stable to light or air, or if other materials such as water vapor otherwise distort the results of the test, a coverslip or envelope may also be used to protect it.

In practicing the method of the invention using this simplified device (diffusion layer/reagent/microparticulate/backing) the person or location to be measured for exposure is provided with the device, and the reagent at the surface of the microparticles traps the gas during the period of exposure.

The manner of entrapment and of progress of the gas toward the reagent is indicated in FIG. 1. As shown in FIG. 1, for the device of the invention, the gas analyte particles, C, are faced with a constant diffusion layer thickness in order to reach the reagent. Each additional C molecule has the same path to travel as the previous one.

Figure 2:
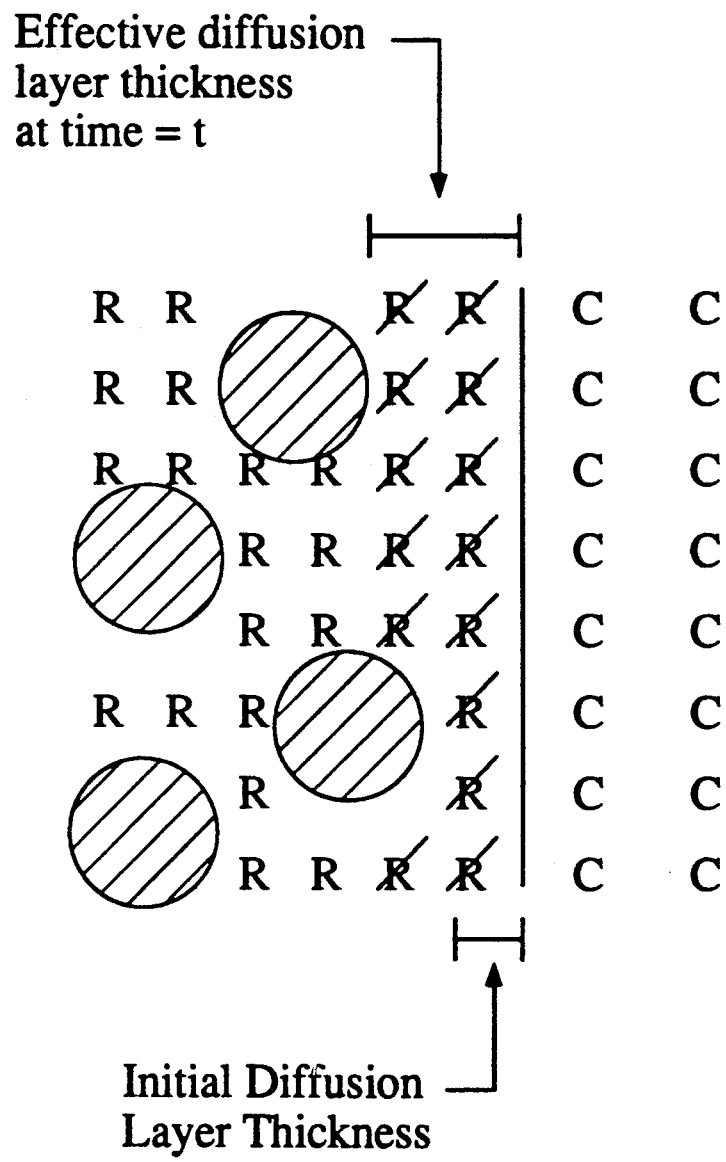
FIG. 2 shows a detection device designed according to prior art devices containing microparticles in a sea of collection layer.

This behavior differs from previously constructed devices wherein the microparticles are distributed in a sea of reagent and a polymer comprising the diffusion layer. As shown in FIG. 2, as time progresses, the reagent at the surface of the sea is used up, and the gas molecules have a longer and longer path of diffusion in order to find reagent with which they can react. Under these circumstances, as described in U.S. Pat. No. 4,436,819, the response/concentration ratio does not maintain itself over extended time periods, but decreases with the square root of time.

U.S. Pat. No. 4,436,819 explained how, under certain exceptional situations, Case II diffusion could result in a device similar to that of FIG. 2 acting as a true dosimeter due to continuous swelling of the diffusion moderator in response to the advance at high levels of a gaseous penetrant. Under these circumstances, as set forth in U.S. Pat. No. 4,436,819, as time progresses, the gas molecules penetrate the swollen outer layer of the reagent diffusion layer, being limited by a diffusion layer only as they near the location of unused reagent and unswollen diffusion moderator. This is illustrated in FIG. 3 which shows that the devices comprising particles distributed in a sea of reagent/binder exhibit true dosimetry only if the effective barrier of the sea recedes as rapidly as the zone of consumed reagent. Thus, at any arbitrary time t, the diffusion layer thickness has not changed. Case II diffusion, however, cannot be operative at low penetrant concentrations. Case II diffusion can only be achieved with the devices of FIG. 2 at these low concentrations by presenting a constant diffusion layer artificially by use of a cover as shown in FIG. 4.

In that case, the cover provides a constant penetration requirement while providing reagent in the enclosed binder C. However, this device works only at low concentrations which do not use up the surface layer of reagent in the enclosed reagent pad.

Thus, the measurement and absorption of the analyte by the device of the present invention depends on the specific configuration wherein a constant diffusion layer is provided surrounding the reagent-coated particles.

When the dosimeter has been exposed for the desired time period, it is removed from the environment to be monitored and the response measured in a manner appropriate to the particular gas analyte, the reagent selected, and the configuration of the device. If the device has been enclosed in an encapsulating envelope, it may need to be removed to effect color development; the device can then, if desired be replaced in the envelope. On the other hand, if the device is of the form shown in FIG. 5 and contains a cover slip, the cover slip may automatically be lifted when the remainder of the device is placed in contact with secondary reagent and the slip may then be replaced for reading reflectance for example, in the especially designed carrier of FIG. 7.

Thus the details of the remainder of the procedure depend on the nature of the particular chemistry employed. In the easiest possible case, if a specific reagent can be found which results in a detectable product that is stable over time, no further treatment is necessary. However colored products are notorious for their instability, and the exposure times required by the low levels of analyte are often quite long, thus, more commonly, the reagent-analyte product is further developed by contact with a developing solution. In practice, the device is after the required exposure time conveniently dipped into a solution which contains an additional reagent required for the formation of color. Thus, in this case, the reaction takes place in two steps—a specific reagent in the collecting layer stores the analyte in an intermediate form, and one or more reagents in the developing solution convert the intermediate to colored product. In any event, once the colored product is obtained it can be quantified by placing the device in a suitable sample holder so that the intensity of a reflected beam can be compared with that of an incident beam.

Figure 7:
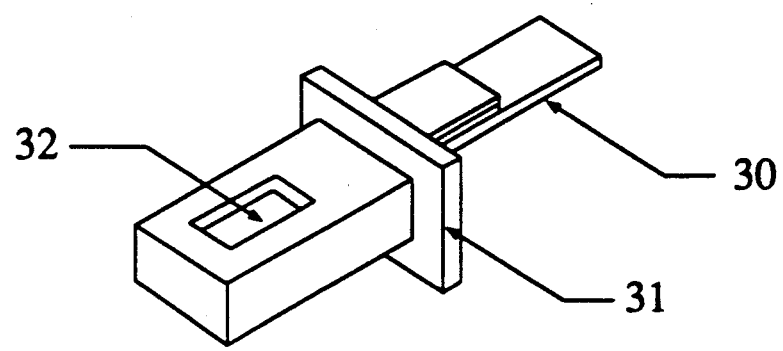
FIG. 7 shows a sample holder for reading the reflectance of the device.

Such reflectance measuring devices are well known in the art such as the Model 5580 Glucometer (Ames Division. Miles Laboratories) and are commercially available. In application to this invention, the reflectance meter serves, in effect, to measure the absorbance of light by the sample at a particular wavelength over a double path length traveled first by the incident and then by the reflected beam through the collection layer sample holders for convenient configurations of the device of the invention are also commercially available. A holder designed to accommodate a rectangular strip particularly useful for this device is shown in FIG. 7. The holder is basically a plastic carrier which contains an oblong enclosure 33 for insertion of the device 30. A window 32 permits the surface of the device to be exposed to light and reflectance to be measured; the flange 31 permits easy positioning in an instrument with a cavity into which the department 33 is placed.

The foregoing description is sufficient to describe the features of the device when the detectable product is not decomposed by air, by ultraviolet light or by removal of solvent, or where interfering substances such as water vapor are not present. However, if the detectable product is unstable, or there are interfering materials in the test environment it is advantageous to place over the collection layer some type of transparent protective cover.

Figure 5:
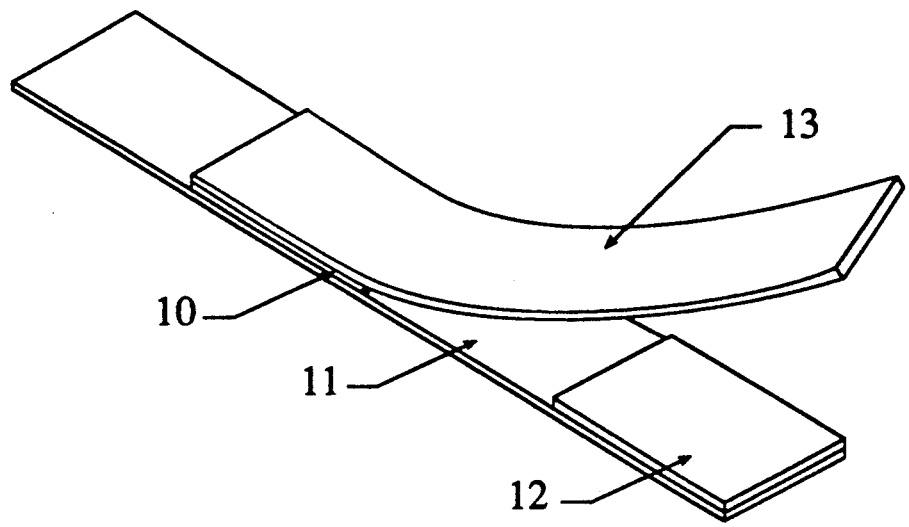
FIG. 5 shows the device of the invention having a protective coverslip.

One type of such protection is a cover slip which protects against rapid diffusion of air, against penetration of ultraviolet light, against solvent loss and against the penetration by water vapor. This cover slip must of course, be transparent in order to be adaptable to the foregoing procedure. Also, it must be sufficiently flexible so as to permit the developing solvent to make contact with the entire layer of coated microparticles and then prevent air intrusion and solvent loss. A convenient configuration to accomplish this is shown in FIG. 5. As shown there, a transparent cover slip 13 extends over the layer containing the coated microparticles 12 coated on the backing 11 but is attached securely 10 to the backing. When the device is dipped into a developing solution, the cover slip separates from the collection layer thus permitting the solvent to make contact. When it is removed, it can be pressed once again against the layer containing coated particles to provide the desired protection. The portion of the device containing backing, layer of particles and cover slip is then placed in a suitable container such as that of FIG. 7 for a reflectance instrument as described above. Whether or not the cover slip is necessary is, of course, entirely dependent upon the chemistry of the detection reaction.

Figure 8:
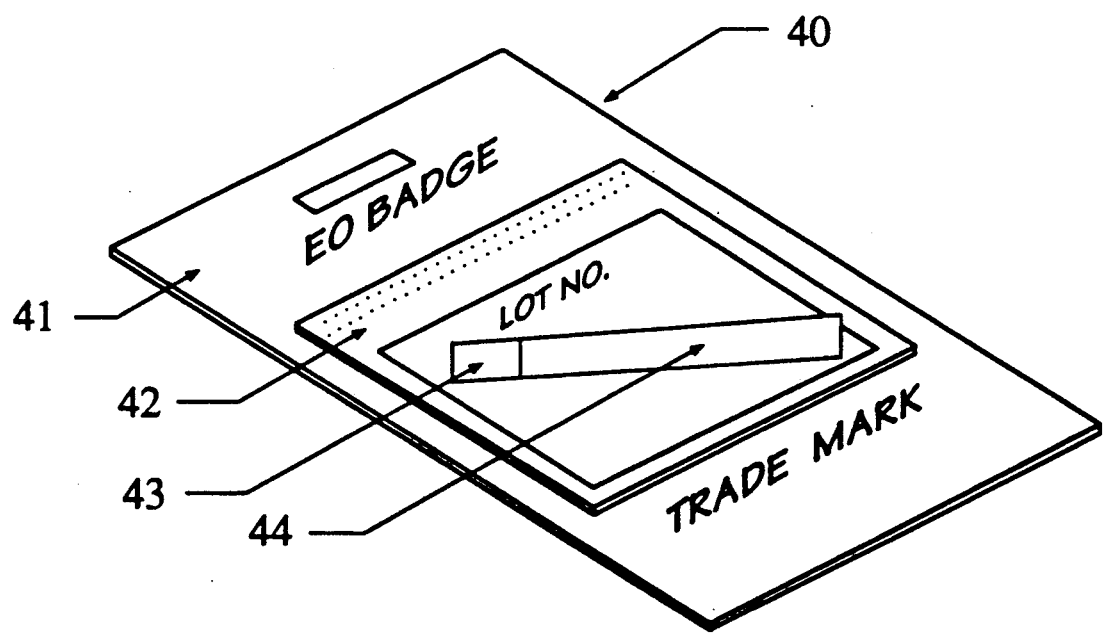
FIG. 8 shows the device having an encapsulating envelope.

Similarly, the entire device may be encapsulated within a plastic envelope which is relatively permeable to the contaminant of interest and relatively impermeable to other substances which might interfere with the assay as shown in FIG. 8.

C. Detailed Description of the Device

In general, the device consists of a backing on which are disposed microparticles coated at the surface with a reagent and in turn surrounded by a diffusion layer, and, where made desirable by the chemistry, a cover slip or encapsulating envelope.

Suitable materials for the backing are hard, flat surface relatively thin reflecting polymers such as polystyrene pigmented with $TiO_2$ or polyesters which have then extruded into flat sheets. A particularly preferred backing is a polystyrene-$TiO_2$ pigmented matte finish backing such as that commonly found in graphic art applications.

Bound to the backing are adsorbent, reflectant particles for support, which are coated with a reagent at their surface, in turn surrounded by a diffusion layer which comprises diffusion moderator a binder and, optionally, a plasticizer.

Suitable microparticulate adsorbents ace particulate solids which have surface areas of at least 10 $m^2/g$, preferably 100–1000 $m^2/g$. These materials usually have a particle size of 100 microns or less, i.e., 0.1–100 microns. Materials which are available in this form include inorganic refractory oxidic supports, such as alumina, silica, glass titania, clays and the like, or organic polymers which have been treated to achieve porosity. e.g., porous cellulose, polypropylene, and polystyrene-divinylbenzene particles. In order to be compatible with a detection reaction which generates color, the support must be essentially colorless. In addition, these supports can be further manipulated chemically so as to change their polarity characteristics. For example, if silica gel is used the hydroxyl groups of the silica can be derivatized with organic molecules to create a more inert and lipophilic adsorbent.

The reagents used to coat the particles are discussed in a separate section below.

As to the diffusion moderator and binder virtually all binders are diffusion moderators but not all diffusion moderators are binders. Any high molecular weight material capable of forming a film can serve as a diffusion moderator, therefore this purpose can be served by, for example, silicone and mineral oils, polyoxyethylenes, and fatty acid esters. These are, however generally not adhesive and do not serve as binders. Suitable diffusion moderators which can also serve as binders include ether derivatives of cellulose such as, for example, hydroxypropyl or hydroxyethyl cellulose: or ester derivatives such as cellulose acetate, cellulose propionate, or cellulose butyrate. Also suitable are mixtures of polyacrylic acid and polyacrylamides, including hydroxylated polyacrylamides.

Suitable plasticizers include polyethylene glycol (PEG). polypropylene glycol (PPG) and various phthalate esters such as the dibutyl, or dioctyl esters.

The nature of the specific reagent depends, of course, on the material to be measured and is discussed in paragraph D below.

In general, the microparticulate support/collection layer contains approximately 75–80% by weight of the adsorbent support, about 5–15% by weight of diffusion moderator/binder and less than 5% plasticizer. Approximately 10% or less of the support/collecting layer is the specific reagent. The foregoing percentages and ranges of course, are approximate and are intended not to be limiting but to indicate the general range of preferred operability. At these ranges individual microparticles are coated with collection layer; insufficient weight of layer materials is present to permit a "sea" in which the particles float. Calculations conducted in connection with designing chromatography supports indicate for example, that a total Weight % of about 12% is required for particles of about 200 $m^2/g$ and about 24% for particles of about 400 $m^2/g$. Thus, for the ranges contemplated herein, each particle is surrounded by a collection layer rather than being "at sea".

Where its use is appropriate, the cover slip is composed of a commonly available transparent plastic such as, for example, a thin-layered polyester such as 0.005 inch thick polyester materials, for example, Mylar ®. Such coverslips are readily available commercially, as they are frequently used in graphics to encase works of art. Suitable adhesives for attaching the coverslip to the reflectant support are also commercially available. A particularly preferred adhesive is a proprietary acrylamide-acrylic acid formulation available from 3M Company as a transfer tape. The adhesive can simply be rolled onto the plastic support from its backing and the tape backing then removed. The edge of the coverslip is then pressed against the adhesive strip that has been applied.

When an encapsulating envelope is desirable, a polyethylene or polypropylene encasement of the entire device may be used as shown in FIG. 8. These materials, for example, are quite permeable to test substances such as ethylene oxide, but less so to water, polar materials and particulates.

D. Specific Reagents and Chemistries

Each gaseous substance desired to be quantified will have a characteristic specific reagent and associated chemistries appropriate to it. In most cases presently known both a specific reagent and a developing reagent are required since the ultimate detection product is characteristically less stable than the intermediate formed by reaction of the gas with the specific reagent. However the device is equally applicable to chemistries which provide stable detection products retaining their characteristic light absorption properties over the period of exposure.

Some specific examples of workable chemistries follow:

Ethylene oxide can be detected by reaction with 4-(4-nitrobenzyl)pyridine at high PH. The use of this reaction to generate color when associated with nitrocellulose was disclosed in U.S. Pat. No. 4,094,642. In the device of the present invention, however the 4-(4-nitrobenzyl)pyridine is coated onto the microparticles and surrounded by the diffusion layer at a relatively low PH. Preferably around 4. Thus, if this system is used, the support/collection layer will preferably comprise 10% of the 4-(4-nitrobenzyl) pyridine, 9% hydroxypropylcellulose as diffusion moderator and binder, 3% PEG as plasticizer, and the remainder alumina which has been washed to its natural pH of approximately 4. (Silica gel is less advantageous in this embodiment as its washed surface has a pH which is disadvantageous for the reaction of the specific reagent (PH 2-3)). No color is developed until the ambient pH is modified. Thus, the color is obtained by dipping the device into a developing solution so that the collecting layer contacts a neutralizing concentration of a suitable base such as, for example, triethylene tetramine triethylene diamine, ethanolamine or Tris. When the color is developed, it can then be read on a reflectance meter. As the color is known to be decomposed by light and air, the device containing the additional coverslip is preferred. Otherwise reading must be made immediately after development.

For measurement of formaldehyde, an operable specific reagent is phenylene diamine adsorbed to the particles supporting the collecting layer. No color is detectable until the layer is contacted with a peroxide solution, whereupon the intensity of the color formed is dependent on the amount of formaldehyde reacted with the phenylene diamine. In this example, as well, the use of a coverslip is preferred. Another reagent suitable for formaldehyde detection is rosaniline which forms a colorless complex with the formaldehyde until contacted with $SO_2$ as the secondary reagent.

The chemistries cited above are, of course, merely illustrative. Analytical reagents which form stable colored products with a variety of other gases, or which form stable intermediates which can be converted into colored products are known in the art and available to practitioners.

E. Detailed Description of a preferred Embodiment

A particularly preferred embodiment of the device of the invention results in rectangular strips containing at one end a coating of the supported collection layer and a protecting coverslip secured to the backing above the supported collection layer by an adhesive. This form of the device is shown in FIG. 5. The rectangular backing, 11, is approximately 2 inches × ¼ inch and has a layer of coated microparticles 12, approximately ¼ inch square at one end. The backing is a polystyrene-$TiO_2$ pigmented matte finish strip of 200-500 microns thickness. The layer 12 is approximately 100-500 microns in depth and contains 78% alumina particles previously washed to a pH of 4 coated with 10% 4(4-nitrobenzyl) pyridine, and then with 3% PEG and 9% hydroxypropyl cellulose. (These percentages represent proportions of the total coated particulate mass.) At the amounts of materials given, the alumina particles which are the majority by weight of this mass are coated thinly with the 4-(4-nitrobenzyl) space pyridine in a single coat and the diffusion layer surrounds the reagent as a thin uniform diffusion layer around each particle. At these typical amounts, the amount of reagent per square meter is of the order of $10^{-4}$ to $10^{-2}$ g/m$^2$, assuming the particle size range of 10-1000 m$^2$/g of particles.

The supported collecting layer 12 is covered by a coverslip, 13, as shown, which is secured to the backing at 10 by an adhesive. The coverslip is 0.005 inch thick polyester and is secured by a strip of transfer adhesive.

This embodiment can measure concentrations of ethylene oxide over the range of 0.1-5000 ppm over a time range of 10 min-10 hrs. Its total absorbing capacity for ethylene oxide is 50 μg. corresponding to an exposure of about 5000 ppm-hr.

The color is developed by contacting the collecting layer with a 1-10% solution of triethylene tetramine by dipping the portion of the strip covered by the layer of coated particles vertically into the solution for 3-5 seconds. The strip is then removed, and the coverslip pressed back into place and wiped with a tissue. The entire sandwich is then placed in a reflectance meter using the holder shown in FIG. 7 so that the layer shows through the opening 32 and the reflectance read. The color is stable over a period of 10-20 min.

F. Method of Manufacture

Figure 6:
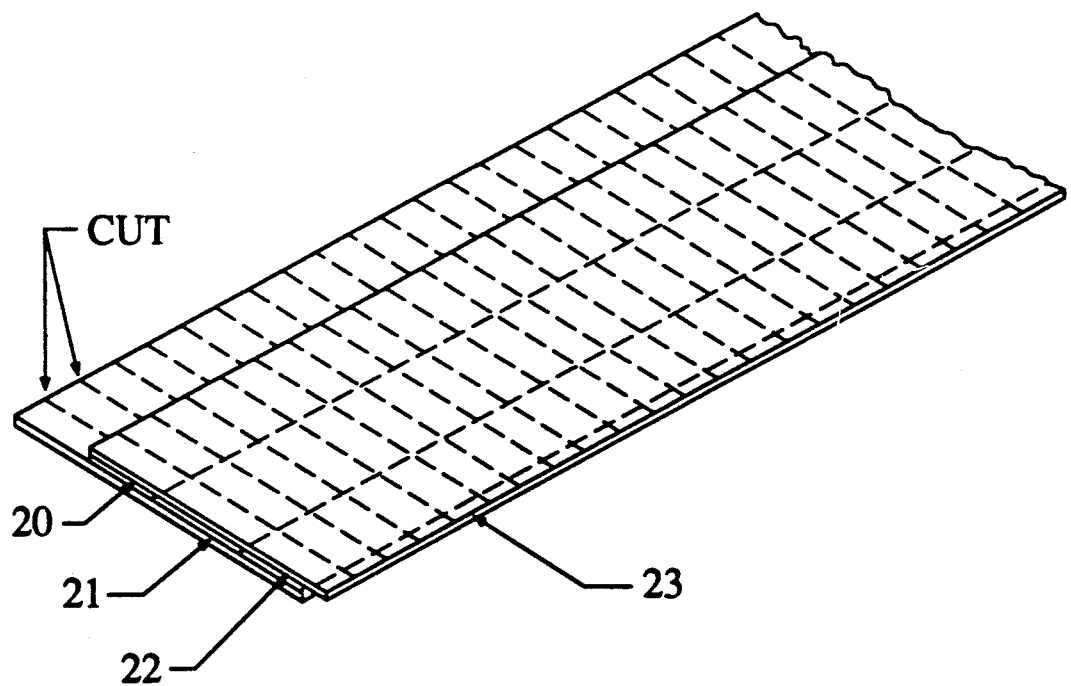
FIG. 6 shows an intermediate stage in the manufacture of the device.

The above-described device is most conveniently made by casting onto a strip of backing approximately 5'×4", a stripe lengthwise along the center of the backing, the stripe being approximately 1" wide. This can be done using a suspension of the coated particles in methanol and employing a commercially available casting machine which rolls the backing strip through so as to lay down the particulate layer as a stripe. FIG. 6 shows the resultant (which has been cut lengthwise in half). The backing 21 shows the particulate layer stripe 22. Two adhesive strips are then applied on either side of the layer stripe lengthwise along the backing in approximately the position shown for one side of the strip at 20 in FIG. 6. The strip is then cut lengthwise in half giving two similar lengthwise portions as shown in FIG. 6. A plastic covering material 23 is applied to the adhesive so that it extends slightly past the end of the collection layer portion of the backing. The support strip is then cut crosswise as shown in FIG. 6 into approximately ¼ inch sections to give approximately 50 of the devices shown in FIG. 5 per foot of material. This method of manufacture represents a highly efficient manner of constructing a large number of such devices at low cost.

If desired, the device of FIG. 5 may be further enclosed within an envelope as depicted in FIG. 8 to afford further protection from interfering substances as described earlier. In such cases. enclosure may be made at low cost via the use of commercially available automated packaging machines such as those manufactured by Circle Design Co. The cover slip and the envelope are alternative means to protect the microparticulate layer from contamination, including contamination by water vapor which is probably the most serious problem encountered in devices of this type. Water vapor is a major contaminant in all environments in which personal exposure monitoring is conducted. For example, 10% relative humidity equates to more than 5,000 ppm water in the air, which is a level 5,000 times higher than the maximum permissible workplace level for ethylene oxide, for example. It is known that adsorption of significant quantities of water by collection media such as charcoal, silica, paper, and alumina lower that media's affinity for the contaminant of interest and may thus change its uptake rate during measurement. Therefore, any sampling device in order to maintain proper accuracy must take account of this effect. In the devices of the invention, semipermeable diffusion moderator applied to the reagent particles and, in some cases, the encapsulating envelope serve as a moisture filter as well as protecting the sampling layer from gross particulate contamination and, in some instances, the effect of light of particular wavelength.

We claim:

1. A process for manufacturing a test strip useful for quantifying time weighted average exposure to a gaseous substance which process comprises:
 casting onto the surface of a rectangular sheet of reflectant, nonporous, planar backing, a layer of reflectant adsorbent microparticles wherein said microparticles are coated at their surface with a reagent specifically reactive with the gaseous substance to be quantified and wherein said reagent coated particles are further coated with a diffusion layer which permits diffusion of the gaseous substance through it to contact the specific reagent at the surface.

2. A test strip prepared by the process of claim 1.

3. The test strip of claim 2 wherein the diffusion layer comprises a diffusion moderator and a binder, which diffusion moderator and binder may be the same or different.

4. The test strip of claim 2 wherein the layer of microparticles is 100-500 microns thick.

5. The test strip of claim 2 wherein the microparticles have a surface are of 10-1000 meter$^2$/gram.

6. The test strip of claim 5 wherein the microparticles comprise 50-85% of the weight of the particular layer.

7. The test strip of claim 2 wherein the detection reagent is a specific reagent for ethylene oxide.

* * * * *